United States Patent [19]

Pittet et al.

[11] Patent Number: 4,613,510
[45] Date of Patent: Sep. 23, 1986

[54] FLAVORING WITH MERCAPTO-C$_2$-C$_3$-ALKANOIC ESTERS

[75] Inventors: Alan O. Pittet, Atlantic Highlands; Ranya Muralidhara, Fair Haven; Manfred H. Vock, Locust, all of N.J.

[73] Assignee: International Flavors & Fragrances Inc., New York, N.Y.

[21] Appl. No.: 784,308

[22] Filed: Oct. 4, 1985

Related U.S. Application Data

[63] Continuation-in-part of Ser. No. 715,344, Mar. 25, 1985, Pat. No. 4,557,941.

[51] Int. Cl.$^4$ ..................... A23L 1/226; A23L 1/235
[52] U.S. Cl. ..................................... 426/535; 560/147
[58] Field of Search ......................... 426/535; 560/147

[56] References Cited

U.S. PATENT DOCUMENTS 4,557,941 12/1985 Pittet et al. ..................... 426/535

*Primary Examiner*—Joseph Golian
*Attorney, Agent, or Firm*—Arthur L. Liberman

[57] ABSTRACT

Described is the genus of mercapto-C$_2$-C$_3$-alkanoic acid esters of citronellol, geraniol, homologues thereof and partially saturated derivatives thereof defined according to the structure:

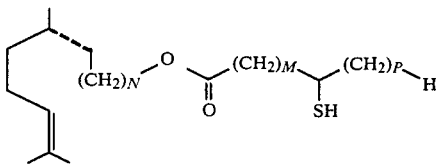

wherein N represents 0 or 1; M represents 0, 1 or 2; P represents 0 or 1; and the dashed line represents a carbon-carbon single bond or a carbon-carbon double bond with the proviso that when N is 0 then the dashed line represents a carbon-carbon single bond uses thereof in augmenting or enhancing the aroma or taste of foodstuffs.

2 Claims, 6 Drawing Figures

NMR SPECTRUM FOR EXAMPLE I.

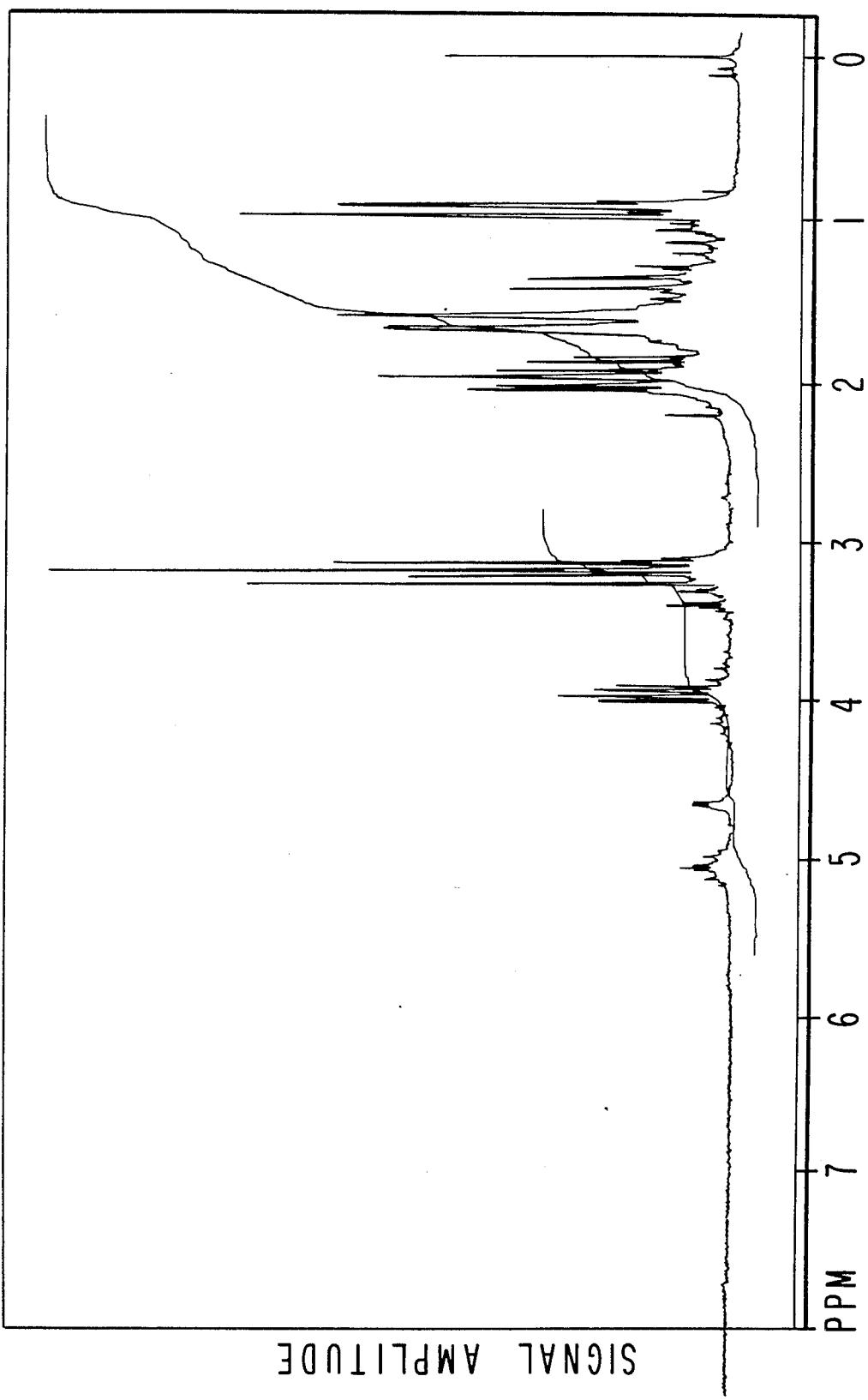

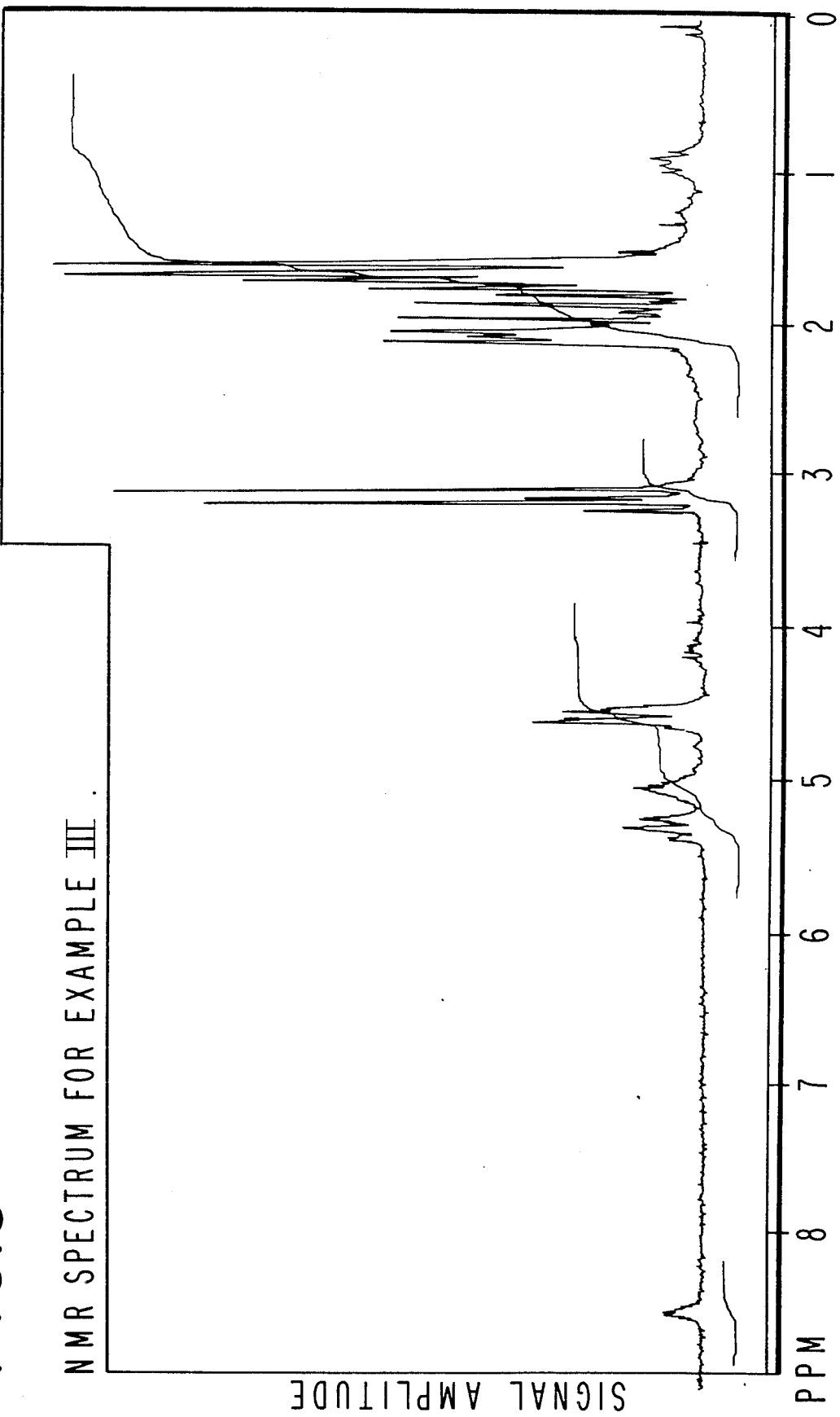

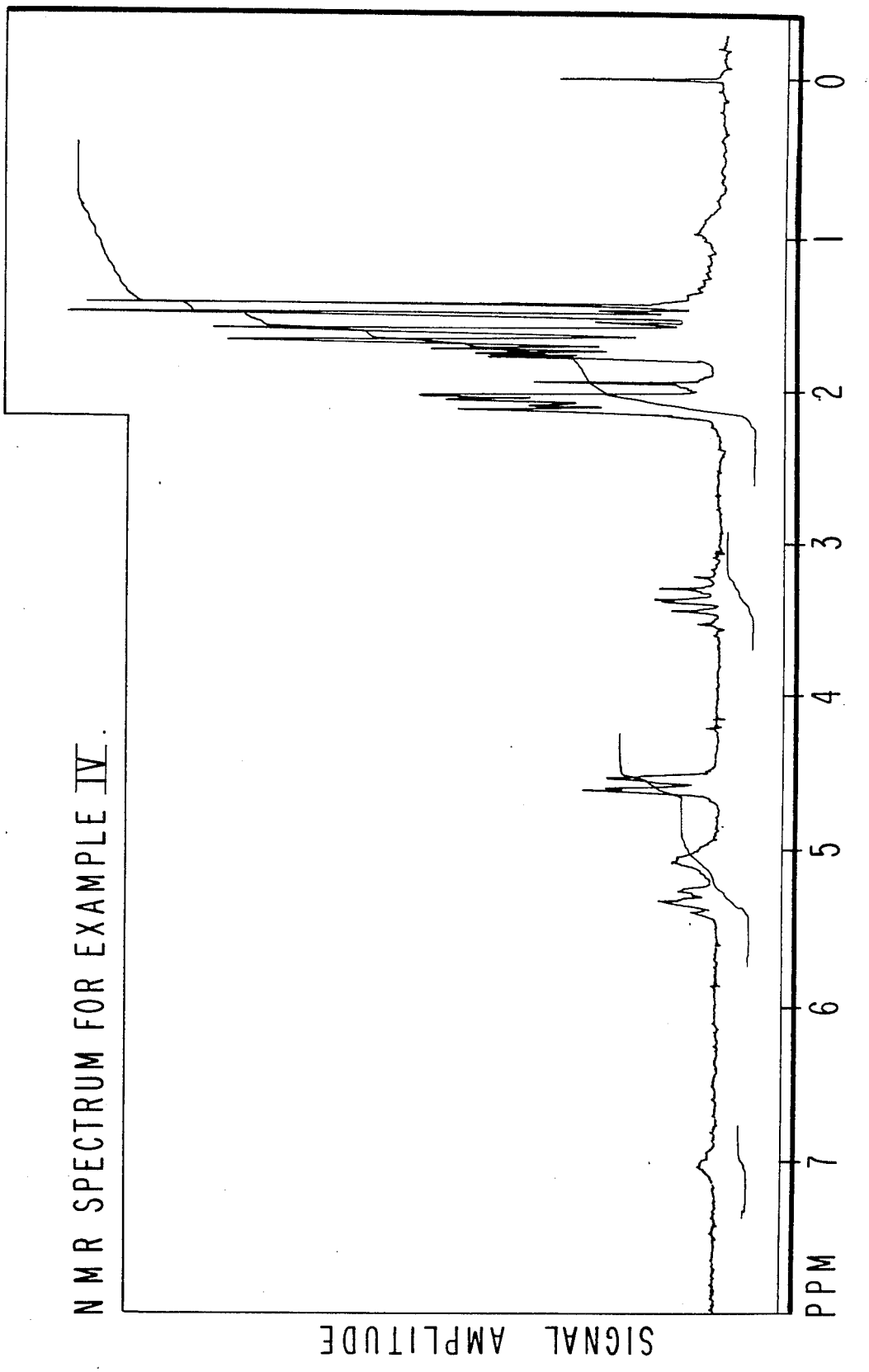
FIG. 4 NMR SPECTRUM FOR EXAMPLE IV.

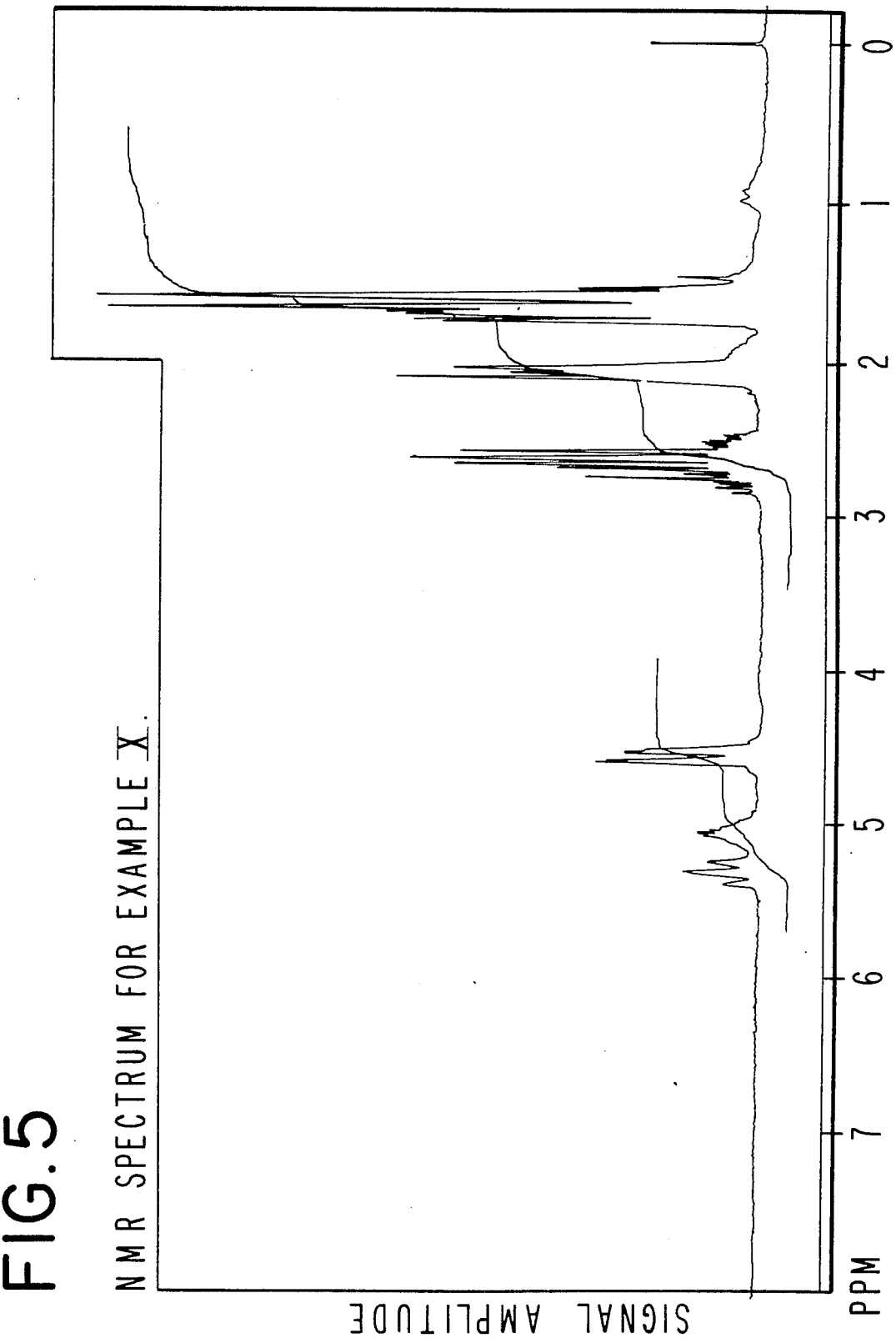

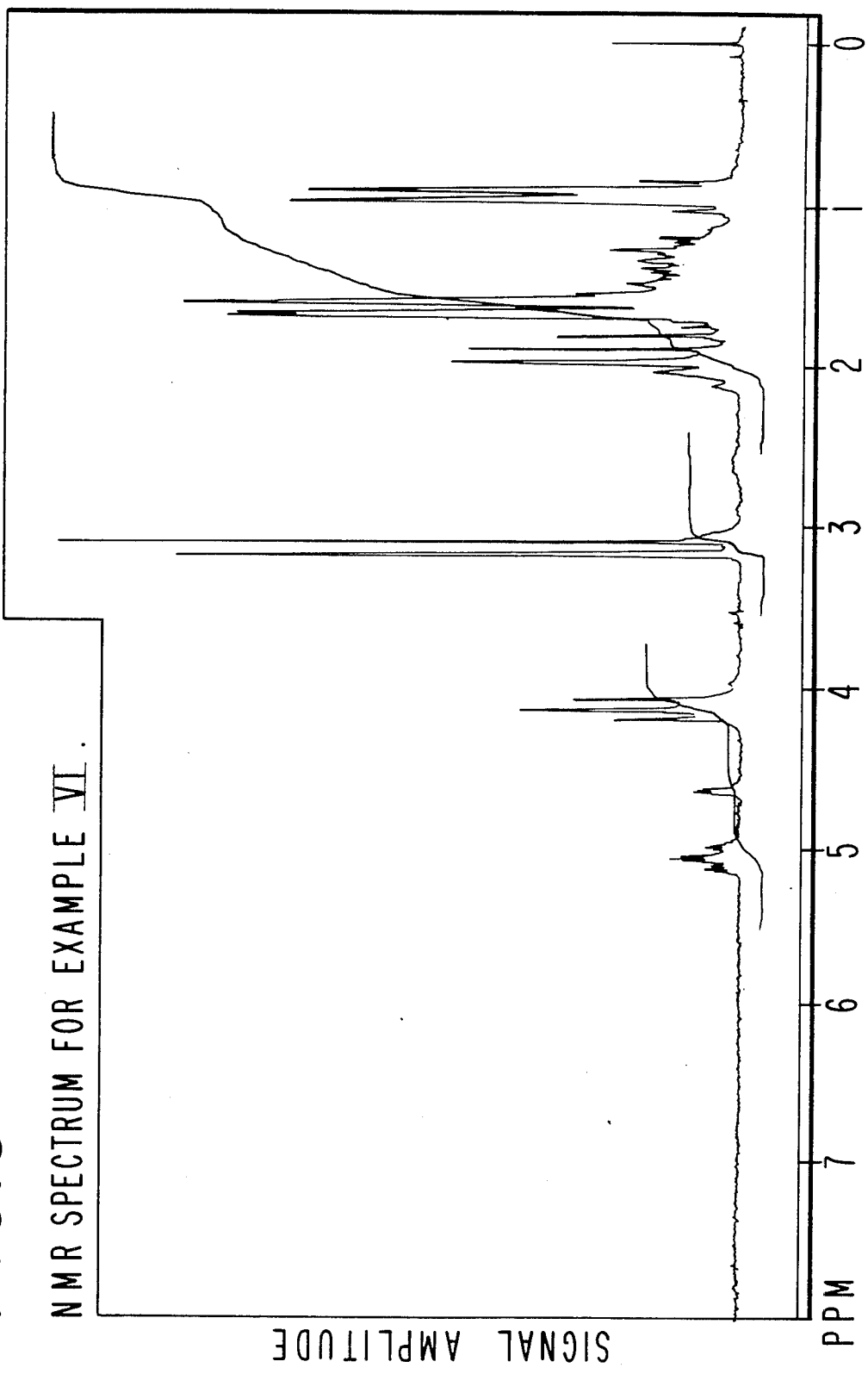
FIG. 6 NMR SPECTRUM FOR EXAMPLE VI.

FLAVORING WITH MERCAPTO-$C_2$-$C_3$-ALKANOIC ESTERS

This application is a continuation-in-part of application for U.S. Letters Patent Ser. No. 715,344 filed on Mar. 25, 1985 now U.S. Pat. No. 4,557,941.

BACKGROUND OF THE INVENTION

This invention relates to mercapto-$C_2$-$C_3$-alkanoic acid esters of citronellol, geraniol, homologues thereof and partially saturated derivatives thereof defined according to the generic structure:

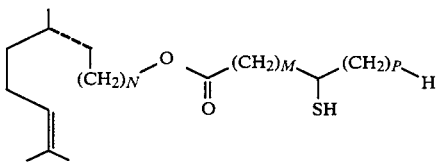

wherein N represents 0 or 1; M represents 0, 1 or 2; P represents 0 or 1; and the dashed line represents a carbon-carbon single bond or a carbon-carbon double bond with the proviso that when N is 0 then the dashed line represents a carbon-carbon single bond and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part, because of the uniform flavor that may be so obtained. For example, natural food flavoring agents such as extracts, essences, concentrates and the like are often subject to wide variations due to changes in quality and type and treatment of the raw materials. Such variations can be reflected in the end product and results in unreliable flavor characteristics and uncertainty as to consumer acceptance and cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having hydrolyzed vegetable protein-like, roasted, sulfury, fruity, concord grape-like, grapefruit, blackcurrant, green, tomato and guava-like aroma and taste nuances.

Reproduction of roasted, sulfury, fruity, concord grape-like, grapefruity-like, blackcurrant-like, green tomato and guava aroma and taste nuances has been the subject of long and continuous searches by those engaged in the production of foodstuffs. The severe shortage of food, especially protein foods, in many parts of the world has given rise to the need for utilizing non-meat sources of proteins and making such proteins as palatable as possible. Hence, materials which will closely simulate or exactly reproduce the flavor and aroma of hydrolyzed vegetable protein and even blackcurrant, tomato, guava, grapefruit, roasted peanut and concord grape are required. Furthermore, meat flavors and vegetable flavors have been enhanced previously by the use of such materials as monosodium glutamate. In many diets, sodium is not desired. Furthermore, in many diets, the use of glutamate ion or glutamic acid is highly undesirable. Therefore, a need has arisen for a monosodium glutamate replacer and an alkali metal glutamate replacer which does not have any glutamate ion or any sodium ion present.

Moreover, there are a great many meat containing or meat based foods presently distributed in a preserved form. Examples of these are condensed soups, dry soup mixes, dry meat, freeze dried or lyophilized meats, packaged gravies and the like. While these products contain meat or meat extracts, the fragrance, taste and other organoleptic factors are often impaired by the processing operation and it is desirable to supplement or enhance the flavors of these preserved foods with versatile materials which have hydrolyzed vegetable protein-like and roasted aroma and taste nuances.

Food flavors in the thioalkanoic acid ester area are known in the art.

Thus, U.S. Pat. No. 4,426,403 discloses the genus of compounds defined according to the structure:

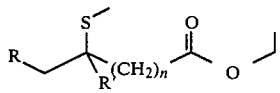

wherein R and R' represent hydrogen or $C_1$-$C_3$ alkyl as food flavorants, particularly in the fruity, vegetable or green pine needle aroma and taste area.

U.S. Pat. No. 3,870,800 relates to the processes for augmenting or enhancing the aroma or taste of foodstuffs using methylthio butanoic acid derivitives. U.S. Pat. No. 3,904,556, at Example XVII thereof states that ethyl-4-(methylthio)butyrate may be added to a cheese sauce to increase the notes usually present in the surface ripened cheese and to increase the cheese flavor intensity. In Example XX it is further stated that this compound, ethyl-4-(methylthio)butyrate is added to tobacco to enhance the pineapple character of a fruit flavor for tobacco.

U.S. Pat. No. 3,879,562 issued on Apr. 22, 1975 and the reissue patent thereof, U.S. Pat. RE No. 30,370 issued on Aug. 12, 1980 disclose the genus of compounds having the structure:

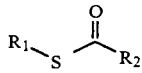

wherein $R_1$ represents alkyl, cycloalkyl, aryl, aralkyl, alkaryl, or alkenyl and $R_2$ represents alkyl, alkyl thioalkyl, aralkyl, alkaryl, or aryl in augmenting or enhancing the aroma or taste of various foodstuffs.

McFadden, et al, Analytical Chemistry 37,560, have suggested the presence of methyl thiohexanoate and thioheptanoate in oil derived from hops, and Buttery, et al, have reported similar work in J. Chromatography 18,399. Schultz, Day and Libbey, "The Chemistry and Physiology of Flavors", Westport, Connecticut:Avi. Publishing Co. 1967, at page 412 disclose thioesters useful in flavoring.

Nevertheless, nothing in the prior art discloses the mercapto-$C_2$-$C_3$-alkanoic acid esters of citronellol, geraniol, homologues thereof and partially saturated derivatives of our invention or their unexpected, unobvious and advantageous uses in augmenting or enhancing the aroma or taste of foodstuffs.

Figure 1:
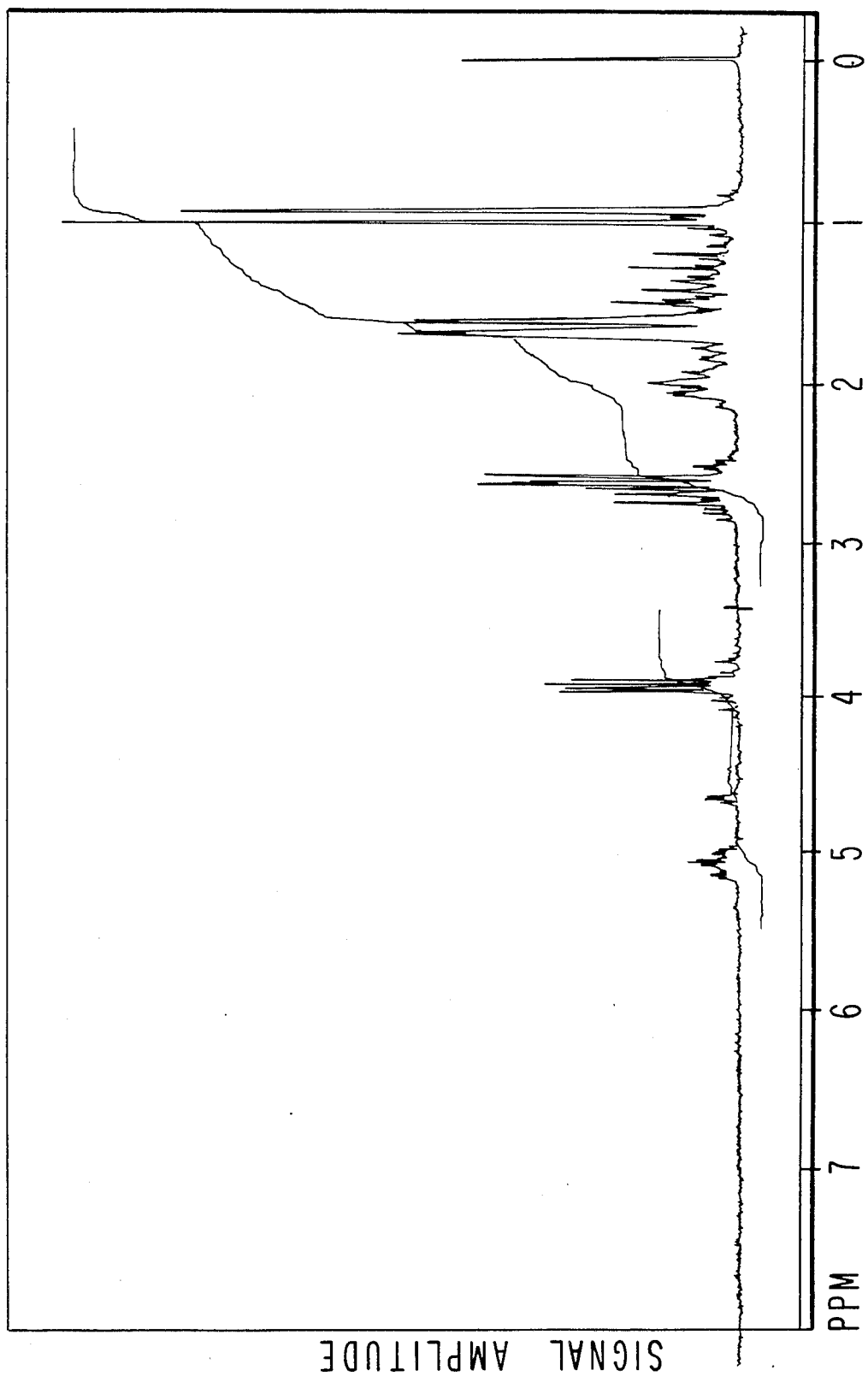
FIG. 1 is the NMR spectrum for the compound produced according to Example I having the structure.

in admixture with the compound having the structure:

(mole ratio:85:15) (Conditions: Field strength: 100 MHz; solvent: CFCl$_3$).

FIG. 2 is the NMR spectrum for the mixture of compounds produced according to Example II having the structures:

and with the mole ratio of the compound having the structure:

to the compound having the structure:

being 85:15 (Conditions: Field strength: 100 MHz; solvent: CFCl$_3$).

FIG. 3 is the NMR spectrum for the compound produced according to Example III having the structure:

(Conditions: Field strength: 100 MHz; solvent: CFCl$_3$).

FIG. 4 is the NMR spectrum for the compound produced according to Example IV having the structure:

("E":"Z" isomer ratio=60:40) (Conditions: Field strength: 100 MHz; solvent: CFCl$_3$).

FIG. 5 is the NMR spectrum for the compound produced according to Example V having the structure:

("E":"Z" isomer ratio=50:50) (Conditions: Field strength: 100 MHz; solvent: CFCl$_3$).

FIG. 6 is the NMR spectrum for the compound produced according to Example VI having the structure:

(Conditions: Field strength: 100 MHz; solvent: CFCl$_3$).

THE INVENTION

The present invention provides mercapto-C$_2$-C$_3$-alkanoic acid esters of citronellol, geraniol, homologues thereof and partially saturated derivatives useful for augmenting or enhancing the aroma or taste of foodstuffs, said mercapto-C$_2$-C$_3$-alkanoic acid esters of citronellol, geraniol, homologues thereof and partially saturated derivatives thereof being defined according to the structure:

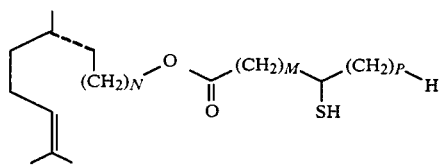

wherein N represents 0 or 1; M represents 0, 1 or 2; P represents 0 or 1; and the dashed line represents a carbon-carbon single bond or a carbon-carbon double bond with the proviso that when N is 0 then the dashed line represents a carbon-carbon single bond as well as methods for augmenting, enhancing or modifying the organoleptic properties, e.g., taste and aroma of said foodstuffs.

The mercapto-$C_2$-$C_3$-alkanoic acid esters of citronellol, geraniol, homologues thereof and partially saturated derivatives of our invention augment or enhance roasted, sulfury, fruity, concord grape, grapefruit, blackcurrant, green tomato and guava aroma and taste nuances making them useful for augmenting or enhancing flavors for such foodstuffs as almond, concord grape, roasted peanut, blackcurrant, tomato, guava and hydrolyzed vegetable protein flavored foodstuffs.

The mercapto-$C_2$-$C_3$-alkanoic acid esters of citronellol, geraniol, homologues thereof and partially saturated derivatives of our invention may be prepared by reacting an alcohol having the structure:

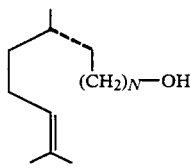

with mercapto alkanoic acid having the structure:

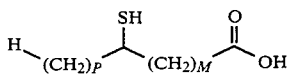

in the presence of a protonic acid such as para-toluene, sulfonic acid or in the absence of such acid at temperatures in the range of from about 100° C. up to about 150° C.; preferably at reflux conditions at atmospheric pressure. Pressures higher than atmospheric pressure may be utilized thereby giving rise to higher temperatures of reaction and shorter time periods of reaction. The time of reaction may vary from about three hours up to about eight hours depending on the temperature of reaction.

Accordingly, the reaction taking place may be shown generically, thusly:

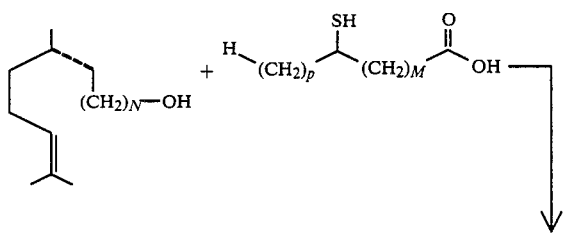

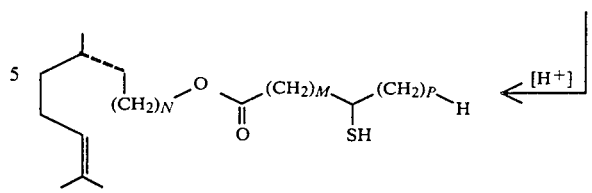

wherein N represents 0 or 1M represents 0, 1 or 2; P represents 0 or 1; and the dashed line represents a carbon-carbon single bond or a carbon-carbon double bond with the proviso that when N represents 0 the dashed line is a carbon-carbon single bond. Examples of alcohol defined according to the structure:

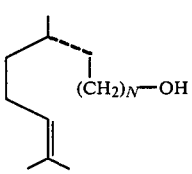

are: Geraniol having the structure:

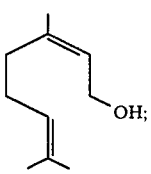

Citronellol having the structure:

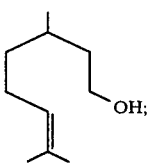

Lower homologues of citronellol are the compounds of a mixture which compounds have the structures, respectively:

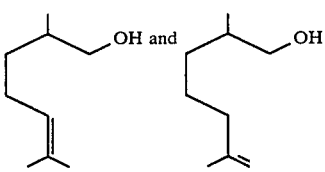

(mole ratio = 85:15).

Examples of mercapto alkanoic acids defined according to the generic structure:

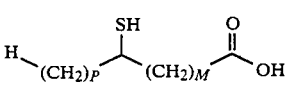

are as follows: 2-Mercapto propionic acid having the structure:

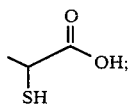

3-Mercapto propionic acid having the structure:

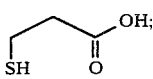

2-Mercapto acetic acid having the structure:

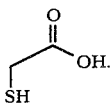

Examples of the products of our invention and their organoleptic properties are as follows:

| Structure of Compound(s) | Organoleptic Properties |
| --- | --- |
| Mixture of compounds having the structures: [structure] and [structure] (85:15) prepared according to Example I. | A roasted sulfury, concord grape aroma and taste profile at 0.1 ppm causing it to be useful in almond, concord grape and roasted peanut flavored foodstuffs. |
| Mixture of compounds having the structures: [structure] and [structure] prepared according to Example II (85:15 ratio, respectively). | A roasted, sulfury aroma and taste profile causing it to be useful in almond and roasted peanut flavored foodstuffs. |
| The compound having the structure: [structure] prepared according to Example III. | A roasted and sulfury aroma and taste profile at 1 ppm causing it to be useful in almond and roasted peanut flavored foodstuffs. |
| The compound having the structure: [structure] prepared according to Example IV. | A grapefruit-like, sulfury, roasted and blackcurrent aroma and taste profile at 1 ppm causing it to be useful in blackcurrent flavored foodstuffs. |
| The compound having the structure: [structure] prepared according to Example V. | A roasted, green tomato, guava and grapefruit aroma and taste profile at 1 ppm causing it to be useful in tomato, guava and hydrolyzed vegetable protein flavored foodstuffs. |
| The compound having the structure: [structure] prepared according to Example VI. | A roasted, concord grape and fruity aroma and taste profile at 0.02 ppm causing it to be useful in concord grape and guava flavored foodstuffs. |

At the end of the reaction as stated, supra, the reaction product is extracted from the reaction mass or the reaction mass is washed, for example, with saturated sodium chloride. The reaction product is then distilled preferably by means of vacuum distillation.

Thus, the mercapto-$C_2$–$C_3$-alkanoic acid esters of citronellol, geraniol homologues thereof and partially saturated derivatives thereof prepared according to our invention can be used to alter, vary, fortify, modify, enhance or otherwise improve the organoleptic properties including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such mercapto-$C_2$–$C_3$-alkanoic acid esters of citronellol, geraniol, homologues thereof and partially saturated derivatives of our invention are accordingly useful in flavoring compositions. Flavoring compositions are herein taken to mean those which contributes a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the mercapto-$C_2$–$C_3$-alkanoic acid esters of citronellol, geraniol, homologues thereof and partially saturated derivatives according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
2-Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein; and
Tetramethyl pyrazine.

The mercapto-$C_2$–$C_3$-alkanoic acid esters of citronellol, geraniol, homologues thereof and partially saturated derivatives or the compositions incorporating them, as mentioned above, can be combined with one or more vehicles or carriers for adding them to the particular product to be flavored. Vehicles can be edible or otherwise suitable materials such as ethyl alcohol, propylene glycol, water and the like. Carriers include materials such as gum arabic, carrageenan, guar gum, xanthan gum and the like. The mercapto-$C_2$–$C_3$-alkanoic acid esters of citronellol, geraniol, homologues thereof and partially saturated derivatives of our invention can be incorporated with the carriers by conventional means such as spray-drying, drum-drying and the like. Such carriers can also include materials for coacervating the mercapto-$C_2$–$C_3$-alkanoic acid esters of citronellol, geraniol, homologues thereof and partially saturated derivatives of our invention (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of mercapto-$C_2$–$C_3$-alkanoic acid esters of citronellol, geraniol, homologues thereof and partially saturated derivatives utilized should be sufficient to impart the desired flavor characteristic to the product, but on the other hand, the use of an excessive amount of the derivative is not only wasteful and uneconomical, but in some instances too large of a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of mercapto-$C_2$–$C_3$-alkanoic acid esters of citronellol, geraniol, homologues thereof and partially saturated derivatives thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The amount of mercapto-$C_2$–$C_3$-alkanoic acid esters of citronellol, geraniol, homologues thereof and partially saturated derivatives thereof of our invention to be utilized in flavoring compositions can be varied over a wide range depending upon the particular quality to be added to the foodstuff. Thus, amounts of one or more derivatives according to the present invention of from about 0.04 ppm up to 80 or 90 percent of the total flavoring composition can be incorporated in such compositions. It is generally found to be desirable to include from about 0.05 ppm up to about 0.1 percent of the mercapto-$C_2$–$C_3$-alkanoic acid esters of citronellol, geraniol, homologues thereof and partially saturated derivatives in such compositions.

The following examples are given to illustrate embodiments of the invention as it is preferred to practice it. It will be understood that these examples are illustrative and the invention is not to be considered as restricted thereto except as indicated in the appended claims.

All parts proportions, percentages and ratios used herein are by weight unless otherwise indicated.

EXAMPLE I

PREPARATION OF THE 3-MERCAPTOPROPIONIC ACID ESTER OF 2,6-DIMETHYL-5-HEPTEN-1-OL

Reaction:

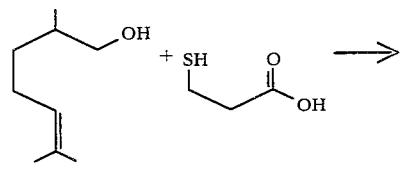

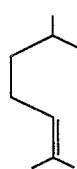

NOTE: Since the alcohol starting material is actually a mixture of isomers having the structures:

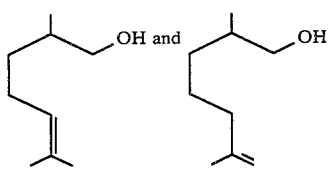

(approximately 85:15 ratio), the resulting product will be a mixture of isomers having the structures:

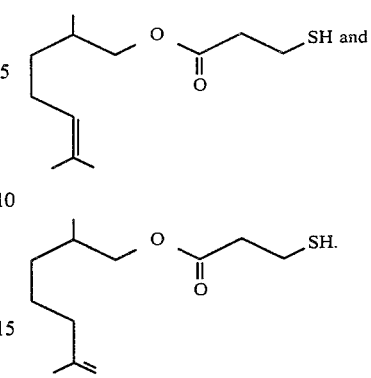

Into a 50 cc flask equipped with 100 ml receiver, reflux condenser, hot plate, stirring bar and magnetic stirring apparatus are placed 16 grams mixture of the compounds having the structures:

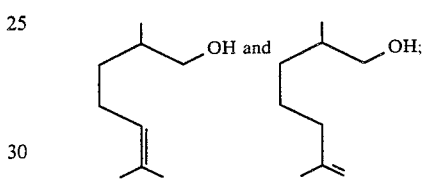

0.2 grams para-toluene sulfonic acid and 2.5 grams of 3-mercaptopropionic acid.

With stirring, the reaction mass is heated to reflux and refluxed for a period of 12 hours. At the end of the 12 hour period, the reaction mass is cooled.

The resulting product is analyzed via NMR, IR and mass spectral analysis.

FIG. 1 is the NMR spectrum of the resulting mixture of compounds having the structures:

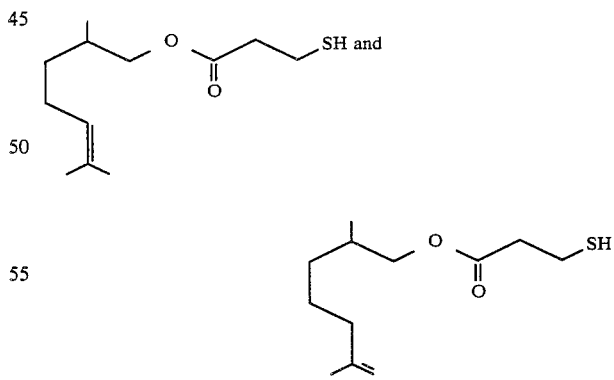

(85:15 ratio respectively).

The resulting mixture of compounds has a roasted, sulfury and concord grape-like aroma and taste profile at 0.1 ppm causing it to be useful in almond, roasted peanut and concord grape flavored foodstuffs.

NMR conditions: Field strength: 100 MHz; solvent: $CFCl_3$.

EXAMPLE II

PREPARATION OF THE 2-MERCAPTOACETIC ACID ESTER OF 2,6-DIMETHYL-5-HEPTEN-1-OL

Reaction:

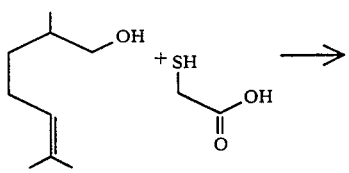

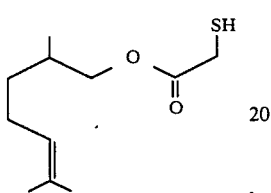

NOTE: Since the alcohol starting material is actually a mixture of compounds having the structures:

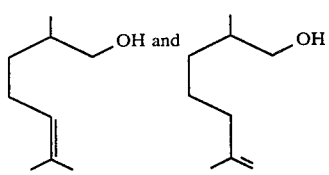

(approximately 85:15 mole ratio), the resulting product will be a mixture of isomers having the structures:

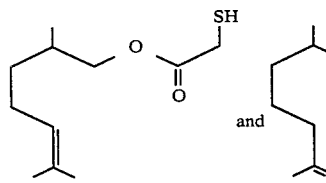

(approximately 85:15 isomer ratio).

Into a 100 ml flask equipped with a 100 ml receiver, heating mantle, reflux condenser, stirring bar and magnetic stirring apparatus is placed 15.5 grams mixture of compounds having the structures:

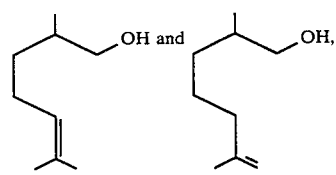

23 grams mercaptoacetic acid and 0.1 grams para-toluene sulfonic acid. The reaction mass is heated to reflux and refluxed for a period of 8 hours. At the end of the 8 hour period, the reaction mass is cooled and fractionally distilled to yield the mixture of compounds having the structure:

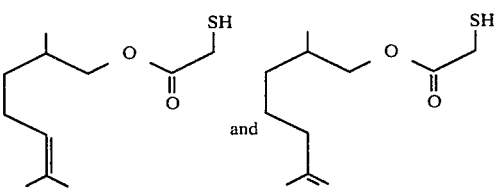

(85:15 mole ratio) as confirmed by NMR, IR and mass spectral analysis.

FIG. 2 is the NMR spectrum for the mixture of compounds having the structures:

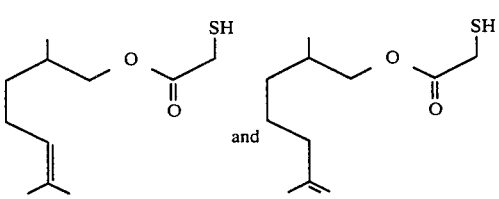

(Conditions: Field strength: 100 MHz; solvent: $CFCl_3$).

The resulting compound has an excellent roasted, sulfury aroma at 0.1 ppm causing it to be useful in roasted almond and roasted peanut flavored foodstuffs.

EXAMPLE III

PREPARATION OF GERANYL MERCAPTOACETATE

Reaction:

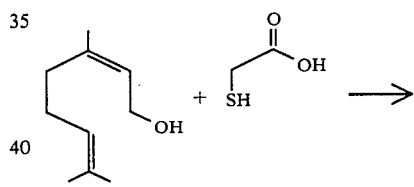

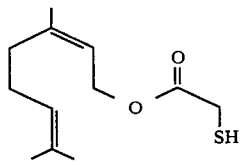

Into a 100 ml flask equipped with hot plate, reflux condenser, stirring bar and magnetic stirring apparatus is placed 38.5 grams geraniol and 9.2 grams mercaptoacetic acid. The reaction mass is heated to reflux and refluxed for a period of 8 hours. At the end of the 8 hour period, the reaction mass is distilled using micro distillation apparatus yielding the compound having the structure:

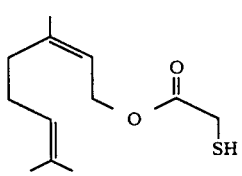

(as confirmed by NMR, IR and mass spectral analysis).

FIG. 3 is the NMR spectrum for the compound having the structure:

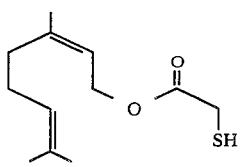

(Conditions: Field strength: 100 MHz; solvent: CFCl₃).
The resulting compound having the structure:

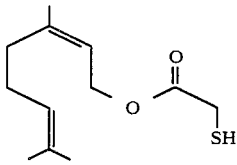

has an excellent roasted and sulfury aroma and taste profile at 1 ppm causing it to be useful for almond and roasted peanut flavored foodstuffs.

EXAMPLE IV

PREPARATION OF GERANYL-2-MERCAPTOPROPIONATE

Reaction:

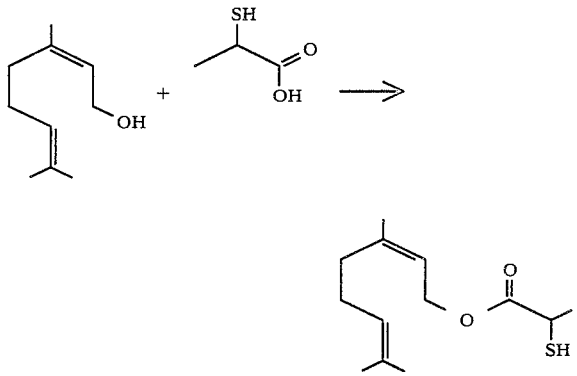

Into a 100 ml reaction flask equipped with hot plate, magnetic stirring bar, reflux condenser, thermometer and 100 ml receiver are placed 49 grams geraniol and 8 grams of 2-mercaptopropionic acid. It is noteworthy that no para-toluene sulfonic acid is added.

The reaction mass is heated to reflux and refluxed for a period of 4.5 hours. At the end of the 4.5 hour period, the reaction mass is distilled on a micro distillation apparatus yielding the compound having the structure:

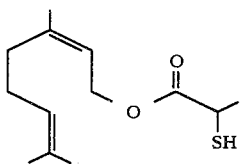

(as confirmed by NMR, IR and mass spectral analysis).

FIG. 4 is the NMR spectrum for the compound having the structure:

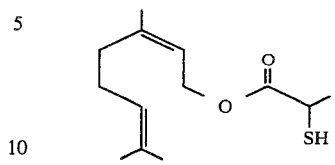

(Conditions: Field strength: 100 MHz; solvent: CFCl₃).
The resulting compound has an isomer ratio which can be described thusly:

"E":"Z"=60:40

The resulting product has a grapefruit-like, sulfury, roasted and blackcurrant-like aroma and taste profile at 1 ppm causing it to be useful in blackcurrant flavored foodstuffs, e.g., blackcurrant jam.

EXAMPLE V

PREPARATION OF GERANYL-3-MERCAPTOPROPIONATE

Reaction:

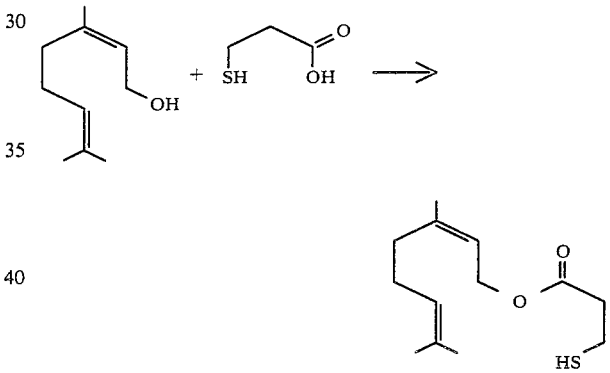

Into a 100 ml flask equipped with magnetic stirring bar, magnetic stirring apparatus, reflux condenser, hot plate and 100 ml receiver are placed 49 grams of geraniol and 16 grams of 3-mercaptopropionic acid.

It is noteworthy that no para-toluene sulfonic acid is added to the reaction mass.

The reaction mass is heated to reflux and maintained at reflux conditions for a period of 6 hours. At the end of the 6 hour period, the reaction mass is distilled using a micro distillation apparatus yielding the compound having the structure:

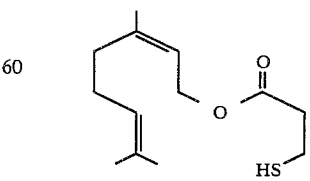

(as confirmed by NMR, IR and mass spectral analysis).
The isomer ratio of the resulting product may be described thusly:

"E":"Z"=50:50

The resulting product has an excellent roasted, green tomato, guava and grapefruit-like aroma and taste profile at 1 ppm causing it to be useful in tomato flavored, guava flavored and hydrolyzed vegetable protein flavored foodstuffs.

EXAMPLE VI

PREPARATION OF CITRONELLYL MERCAPTOACETATE

Reaction:

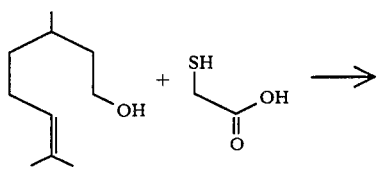

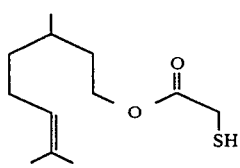

Into a 100 ml reaction flask equipped with magnetic stirring bar, hot plate, magnetic stirring apparatus, reflux condenser and 100 ml receiver are placed 37.5 grams of citronellol, 9.2 grams of mercaptoacetic acid and 0.1 grams of para-toluene sulfonic acid.

The reaction mass is heated to reflux and refluxed for a period of 8 hours. At the end of the 8 hour period, the reaction mass is cooled and distilled on a micro distillation apparatus at a vapor temperature of 115° C., a liquid temperature of 150° C. and a vacuum of 3 mm/Hg pressure.

The resulting product having the structure:

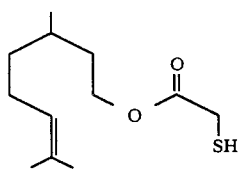

is confirmed as being citronellol mercaptoacetate by NMR, IR and mass spectral analysis.

FIG. 6 is the NMR spectrum for the compound having the structure:

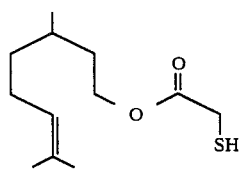

(Conditions: Field strength: 100 MHz; solvent: CFCl₃).

The resulting compound has an excellent roasted, concord grape and fruity aroma and taste profile at 0.02 ppm causing it to be useful in concord grape flavor and guava flavored foodstuffs particularly grape jams and jellies and guava paste, guava jelly and guava nectar.

EXAMPLE VII

Separately, the substances described as follows:

SUBSTANCE "A"

The mixture of compounds having the structures:

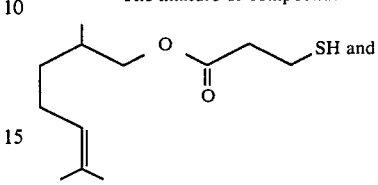

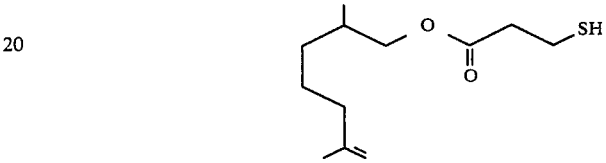

prepared according to Example I;

SUBSTANCE "B"

The mixture of compounds having the structures:

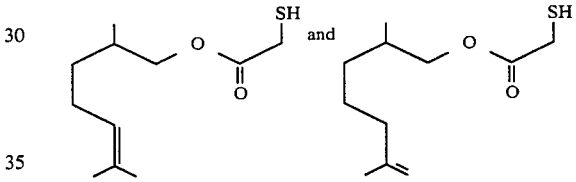

prepared according to Example II; and

SUBSTANCE "C"

The compound having the structure:

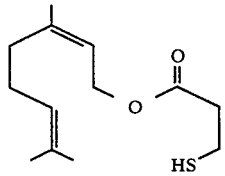

prepared according to Example V are added to 2% solutions of Wyler's "Beef Flavored Instant Bouillon" (manufactured by Wyler Foods, Division of Borden, Inc., Chicago, Ill.) (ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color) at the rate of 1 ppm. Each of the resulting flavors can be described as "beef with excellent roasted, hydrolyzed, vegetable protein-like nuances". The roasted nuances and hydrolyzed vegetable protein-like nuances are enhanced by the addition of the substances prepared according to Examples I, II and V as indicated, supra.

EXAMPLE VIII

At the rate of 0.1 ppm, the mixture of compounds having the structures:

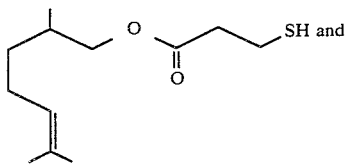

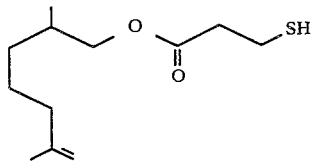

prepared according to Example I and at the rate of 0.02 ppm the compound having the structure:

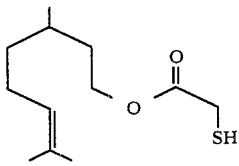

prepared according to Example VI are added separately to SMUCKER'S ® grape jam. Each of the compounds prepared according to Example I and according to Example VI imparts a very natural concord grape nuance to the grape jam causing it to be preferred by a bench panel of five members. Each of the members of the bench panel is employed by International Flavors & Fragrances Inc. the assignee of the instant application. Each of the members of the bench panel did not know the nature of the materials being compared and the meaning of the results ascertained.

EXAMPLE IX

At the rate of 1 ppm, to a CROSSE AND BLACK-WELL ® blackcurrant jam is added the compound having the structure:

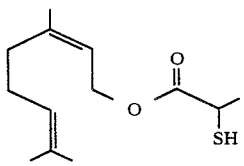

prepared according to Example IV.
The compound having the structure:

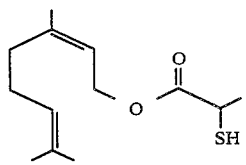

imparts to this blackcurrant jam an excellent grapefruit, sulfury, roasted, natural naunce causing the jam to be much more natural-like and preferred by a bench panel of five members over the jam without the compound having the structure:

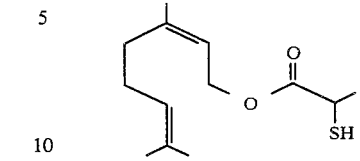

added thereto.

EXAMPLE X

A gravy flavoring material is prepared by admixing the following ingredients:

| INGREDIENTS | PARTS BY WEIGHT |
| --- | --- |
| Diacetyl (5% solution in propylene glycol) | 0.20 |
| Furfural | 0.20 |
| 2-acetyl-3-ethyl pyrazine | 1.00 |
| 2-methyl-3-furfuran thiazole | 0.05 |
| Methional | 2.00 |
| 2,5-dimethyl-3-furan thio acetate | 0.80 |

A bench panel of five individuals compared the above formulation with one additionally containing the compound having the structure:

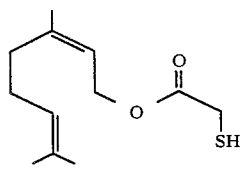

prepared according to Example III which is added at the rate of 5 ppm.

The flavor with the compound having the structure:

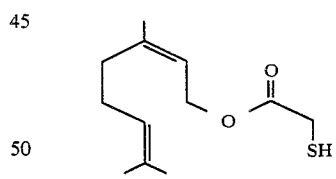

has a roasted, meaty aroma and taste profile with pleasant savory nuances.

When the flavor which includes the compound having the structure:

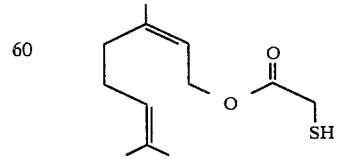

is added at the rate of 0.5% to a standard chicken frankfurter containing 50 parts by weight of chicken and 50 parts by weight of pork, the chicken nuances are intensified 50% more than without the compound having the structure:

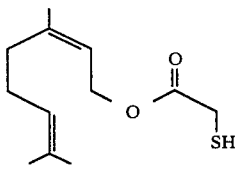

and, in addition, roasted and meaty nuances are imparted.

What is claimed is:

1. A process for augmenting or enhancing the aroma or taste of a foodstuff comprising the step of intimately admixing with said foodstuff at the rate of from about 0.001 ppm up to about 250 ppm of an approximately 85:15 ratio of a mixture of

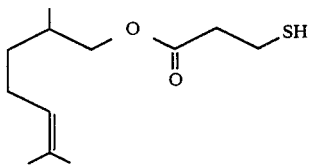

and

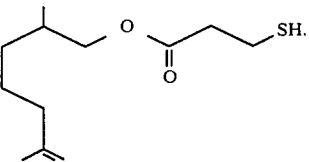

2. A process for augmenting or enhancing the aroma or taste of a foodstuff comprising the step of intimately admixing with said foodstuff at the rate of from about 0.001 ppm up to about 250 ppm of an approximately 85:15 ratio of a mixture of

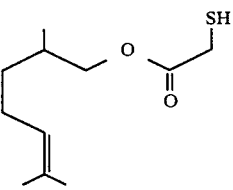

and

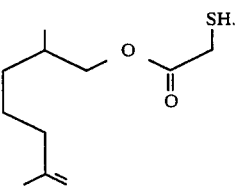

* * * * *